US009085378B2

(12) United States Patent  (10) Patent No.: US 9,085,378 B2
Tsaur  (45) Date of Patent: Jul. 21, 2015

(54) TUBE FILLING PROCESS FOR LIQUID FILLED COTTON SWABS

(75) Inventor: Garry Tsaur, Rowland Heights, CA (US)

(73) Assignees: UNIDOSE SYSTEMS, INC., Racho Cucamonga, CA (US); SWABPLUS, INC., Racho Cucamonga, CA (US)

( * ) Notice: Subject to any disclaimer, the term of this patent is extended or adjusted under 35 U.S.C. 154(b) by 0 days.

(21) Appl. No.: 10/849,085

(22) Filed: May 18, 2004

(65) Prior Publication Data

US 2005/0257498 A1  Nov. 24, 2005

(51) Int. Cl.
B65B 3/00 (2006.01)
A61F 13/40 (2006.01)

(52) U.S. Cl.
CPC .............. *B65B 3/003* (2013.01); *A61M 35/006* (2013.01)

(58) Field of Classification Search
CPC .......................... A61M 35/006; A61M 35/003
USPC .................... 53/410, 412, 432, 469, 474, 467
See application file for complete search history.

(56) References Cited

U.S. PATENT DOCUMENTS

| | | | | |
|---|---|---|---|---|
| 1,641,408 A * | 9/1927 | Bainbridge et al. | .......... | 383/205 |
| 1,705,256 A * | 3/1929 | Krusi | ................. | 604/2 |
| 2,663,461 A * | 12/1953 | Brown | ............... | 53/469 |
| 3,255,494 A * | 6/1966 | Bloch et. al. | ................. | 19/145.3 |
| 3,256,674 A * | 6/1966 | Rutherford | .................... | 53/282 |
| 3,324,855 A * | 6/1967 | Heimlich | .......................... | 604/3 |
| 3,369,543 A * | 2/1968 | Ronco | .............................. | 604/2 |
| 3,481,676 A * | 12/1969 | Schwartzman | ............... | 401/134 |
| 3,661,666 A * | 5/1972 | Foster et al. | .................... | 156/69 |
| 3,757,782 A * | 9/1973 | Aiken | ................. | 604/3 |
| 3,774,609 A * | 11/1973 | Schwartzman | .................... | 604/3 |
| 3,958,571 A * | 5/1976 | Bennington | ...................... | 604/3 |
| 4,415,288 A * | 11/1983 | Gordon et al. | ................ | 401/132 |
| 4,498,796 A * | 2/1985 | Gordon et al. | ................ | 401/132 |
| 4,747,719 A * | 5/1988 | Parkin | .......................... | 401/132 |
| 4,795,421 A * | 1/1989 | Blasius et al. | ..................... | 604/1 |
| 4,863,422 A * | 9/1989 | Stanley | ............................ | 604/3 |
| 5,016,651 A * | 5/1991 | Stalcup et al. | ................ | 128/898 |
| 5,035,348 A * | 7/1991 | Seifert | .......................... | 222/107 |
| 5,152,742 A * | 10/1992 | Simpson | ........................ | 604/3 |
| 5,702,035 A | 12/1997 | Tsao | | |
| 5,762,494 A * | 6/1998 | Archambault | ................. | 433/80 |
| 5,791,801 A * | 8/1998 | Miller | ........................... | 401/132 |
| 5,996,780 A * | 12/1999 | Gurrera | ........................ | 206/209 |
| 6,186,971 B1 * | 2/2001 | Naughton | ......................... | 604/2 |
| 6,405,735 B1 * | 6/2002 | Dockery | ....................... | 132/74.5 |
| 6,406,451 B1 * | 6/2002 | Rowe | ................................ | 604/1 |
| 6,484,908 B1 | 11/2002 | Tsaur | | |
| 6,494,856 B1 * | 12/2002 | Zygmont | ......................... | 604/1 |

(Continued)

*Primary Examiner* — Stephen F Gerrity
*Assistant Examiner* — Eyamindae Jallow
(74) *Attorney, Agent, or Firm* — Christie, Parker & Hale, LLP

(57) ABSTRACT

A tube filling process comprising the steps of loading empty plastic tubes into a fixture, sealing one end of said plastic tubes, cutting a score line on said plastic tubes, filling a first substance into said plastic tubes, removing excess amount of said first substance from said plastic tubes to create equal heights of said first substance in said plastic tubes, filling a second substance into said plastic tubes, removing excess amount of said second substance from said plastic tubes to create equal heights of said second substance in said plastic tubes, centrifuge said plastic tubes, and affixing an applicator tip to an end of said plastic tubes. One or more of the steps may be omitted to produce the desired liquid filled cotton swabs.

9 Claims, 1 Drawing Sheet

(56) References Cited

U.S. PATENT DOCUMENTS

| | | | |
|---|---|---|---|
| 6,592,280 B2* | 7/2003 | Petrich et al. | 401/126 |
| 6,726,482 B2 | 4/2004 | Atkins et al. | |
| 6,754,930 B1 | 6/2004 | Tsaur | |
| 6,773,189 B1 | 8/2004 | Tsaur | |
| 6,779,275 B2 | 8/2004 | Tsaur | |
| 6,779,938 B1 | 8/2004 | Tsaur | |
| 6,802,437 B2 | 10/2004 | Tsaur | |
| 6,811,339 B1 | 11/2004 | Tsaur | |
| 6,823,994 B2 | 11/2004 | Tsaur | |
| 6,874,967 B1 | 4/2005 | Tsaur | |
| 7,581,899 B2* | 9/2009 | May et al. | 401/133 |
| 7,637,679 B2* | 12/2009 | May et al. | 401/133 |
| 8,485,356 B2* | 7/2013 | Thorne et al. | 206/361 |
| 8,740,831 B2* | 6/2014 | Wu | 604/3 |
| 2002/0154935 A1* | 10/2002 | Petrich et al. | 401/126 |
| 2003/0175657 A1* | 9/2003 | Atkins et al. | 433/215 |
| 2003/0233063 A1* | 12/2003 | Nakatani | 604/2 |
| 2004/0099543 A1 | 5/2004 | Tsaur | |
| 2004/0253040 A1 | 12/2004 | Tsaur | |
| 2005/0067316 A1 | 3/2005 | Tsaur | |
| 2005/0101007 A1 | 5/2005 | Tsaur | |
| 2006/0113318 A1* | 6/2006 | May et al. | 222/94 |
| 2006/0282035 A1* | 12/2006 | Battisti et al. | 604/1 |
| 2007/0292195 A1* | 12/2007 | May et al. | 401/134 |
| 2008/0119776 A1* | 5/2008 | Wu | 604/1 |
| 2009/0255953 A1* | 10/2009 | May et al. | 222/1 |

* cited by examiner

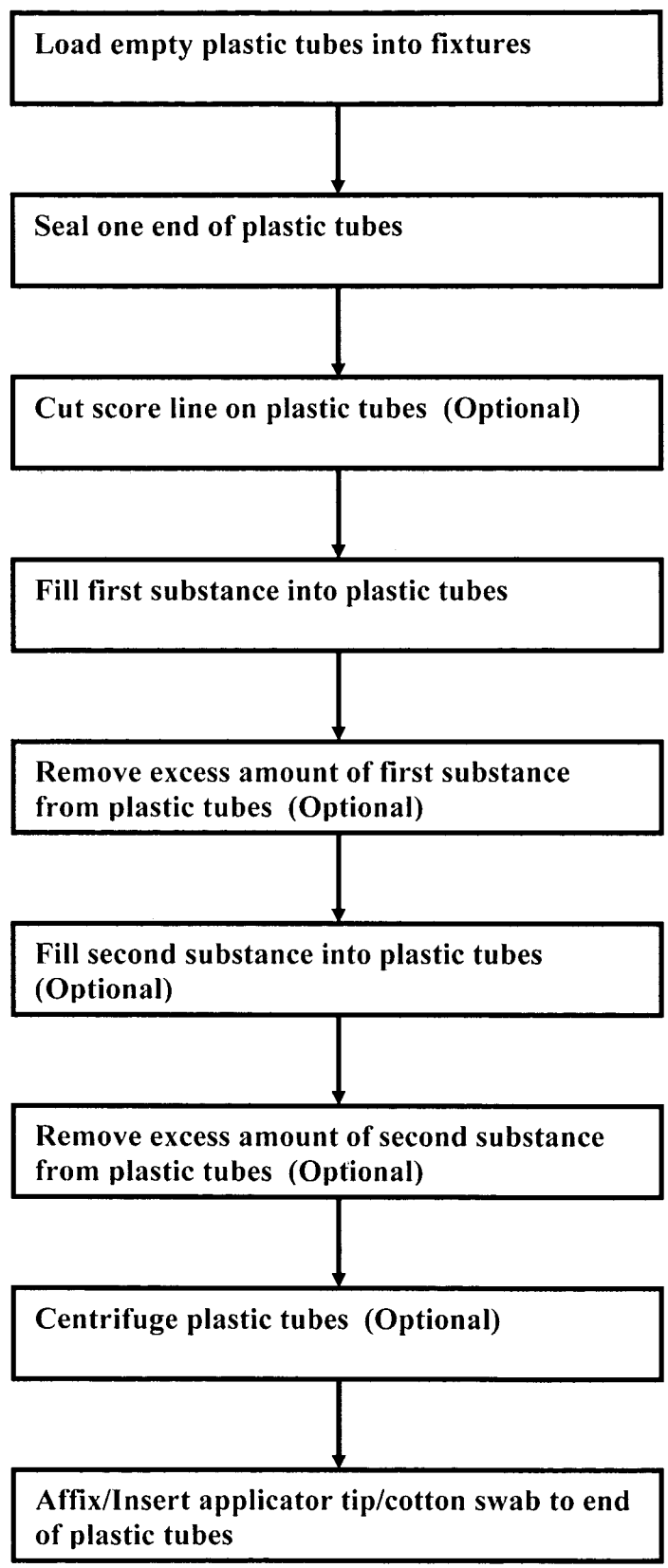

TUBE FILLING PROCESS FOR LIQUID FILLED COTTON SWABS

BACKGROUND-FIELD OF INVENTION

The present invention relates generally to a process for filling small plastic tubes. More specifically, the present invention relates to a process for filling liquid filled cotton swabs with one or more substances.

DESCRIPTION OF RELATED ART

Filling machines and process are generally designed for filling relatively large containers. Various designs of filling machines and process are available for filling containers with volumes ranging from 55 gallon drums to 1 ounce containers for medications. However, there is no known tube filling process that is capable of reliably and accurately filling the extremely small volume inside a very small diameter tube such as a liquid filled cotton swab. The volume inside a liquid filled cotton swab is typically about 0.15 ml. The conventional filling machine and process cannot reliably and accurately fill such a small volume container. Furthermore, conventional filling machines and process are designed to fill only a single substance inside the container.

BRIEF SUMMARY OF THE INVENTION

A tube filling process comprising the steps of loading empty plastic tubes into a fixture, sealing one end of said plastic tubes, cutting a score line on said plastic tubes, filling a first substance into said plastic tubes, removing excess amount of said first substance from said plastic tubes to create equal heights of said first substance in said plastic tubes, filling a second substance into said plastic tubes, removing excess amount of said second substance from said plastic tubes to create equal heights of said second substance in said plastic tubes, centrifuge said plastic tubes, and affixing or inserting an applicator tip to an end of said plastic tubes. One or more of the steps may be omitted to produce the desired liquid filled cotton swabs.

BRIEF DESCRIPTION OF THE DRAWINGS

FIG. 1 shows a flow chart of the tube filling process for liquid filled cotton swabs with all the optional steps.

DETAILED DESCRIPTION OF THE PREFERRED EMBODIMENT

The following description and figures are meant to be illustrative only and not limiting. Other embodiments of this invention will be apparent to those of ordinary skill in the art in view of this description.

The present invention is a process for filling small plastic tubes and liquid filled cotton swabs. The process begins by loading multiple short sections of small diameter plastic tubes with two open ends and with a constant diameter through its length horizontally into one or more fixtures. The small diameter plastic tubes may be fabricated from an extrusion process using polypropylene material and cut to desired length. Each fixture is provided with multiple through holes in it such that one plastic tube will be inserted through each hole. The fixtures allow mass production and automation of the tube filling process.

After multiple plastic tubes are loaded into the fixtures, the plastic tubes are restricted from axial movement such as by placing an end of the plastic tubes against a flat surface. One end of the plastic tubes is then sealed such as by a heat sealing method that melts and seals one end of the plastic tubes. A plug, such as a rubber sealing plug, may also be used to seal one end of the plastic tubes.

A score line may then be formed near the sealed ends of the plastic tubes. The score line may be formed by a shallow cut with a blade around the circumference of the plastic tubes that does not cut through the wall thickness of the plastic tubes. This step may be omitted entirely if a score line is not desired on the plastic tubes. The plastic tubes are then oriented vertically by rotating the fixture ninety degrees.

A first substance, which may be a liquid or other viscous substance, is then injected with a small tube into each of the plastic tubes through the remaining open ends which is now oriented upward. If it is desired to have the first substances in each plastic tube to fill to the same height in each plastic tube for aesthetic or other reasons, the excess amount from a predetermined height of the first substance may be removed by vacuum through another small tube inserted into each plastic tube so that the first substance in all the plastic tubes are of the same predetermined height. The removal of the excess amount of the first substance may also be performed simultaneously as the filling process is being completed.

A second substance may then be injected into each of the plastic tubes on top of the first substance. The second substance may be a different liquid or a viscous substance such as silicone to prevent evaporation of the first substance. Some of the second substance may also be removed if consistent height is desired between the plastic tubes. The removal of the excess amount of the second substance may also be performed simultaneously as the filling process of the second substance is being completed.

The filled plastic tubes may then be centrifuged to remove the air from the substances and to ensure all the substances are near the sealed end of the plastic tubes. The centrifuge may also be performed after filling the plastic tube with the first substance. An applicator tip such as a cotton swab is affixed to or inserted in one end, such as the open end, of the plastic tubes. A second applicator may also be affixed or inserted in the other end, such as the sealed end, of the plastic tubes.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A tube filling process comprising the steps of:
   loading empty plastic tubes into a fixture, said plastic tubes each comprising:
      a first open end; and
      a second open end opposite the first open end;
   sealing closed the first open end of said plastic tubes while the second open end of said plastic tubes remains open throughout the process;
   forming a score line only at the closed end of said plastic tubes;
   filling a first substance into said second open end of said plastic tubes;
   filling a second substance into said second open end of said plastic tubes on top of the first substance; and
   affixing an applicator tip to said second open end of said plastic tubes, wherein the score line is at the closed end of said plastic tubes opposite to said second open end where the second substance is at.

2. The tube filling process as in claim 1, further comprising the step of removing excess amount of said second substance from said plastic tubes to create equal heights of said second substance in said plastic tubes.

3. The tube filling process as in claim 1, further comprising the step of centrifuging said plastic tubes.

4. The tube filling process as in claim 1, further comprising the step of removing excess amount of said first substance from said plastic tubes to create equal heights of said first substance in said plastic tubes.

5. The tube filling process as in claim 4, further comprising the step of removing excess amount of said second substance from said plastic tubes to create equal heights of said second substance in said plastic tubes.

6. The tube filling process as in claim 5, further comprising the step of centrifuging said plastic tubes.

7. The tube filling process as in claim 1, wherein the second substance comprises silicon.

8. The tube filling process as in claim 1, wherein the second substance is a substance that does not evaporate at room temperature.

9. The tube filling process as in claim 1, further comprising the step of affixing another applicator tip to said sealed closed end of each said plastic tubes.

* * * * *